United States Patent [19]
Bhatia et al.

[11] Patent Number: 5,117,008
[45] Date of Patent: May 26, 1992

[54] SOLVENT SCRUBBING RECOVERY OF LACTIDE AND OTHER DIMERIC CYCLIC ESTERS

[75] Inventors: Kamlesh K. Bhatia; Neville E. Drysdale, both of Newark; John R. Kosak, Greenville, all of Del.

[73] Assignee: E. I. Du Pont de Nemours and Company, Wilmington, Del.

[21] Appl. No.: 602,346

[22] Filed: Oct. 23, 1990

[51] Int. Cl.$^5$ .............................................. C07D 319/00
[52] U.S. Cl. .................................................... 549/274
[58] Field of Search .......................................... 549/274

[56] References Cited

U.S. PATENT DOCUMENTS

| | | | |
|---|---|---|---|
| 1,095,205 | 5/1914 | Gruter et al. | 549/274 |
| 2,668,162 | 2/1954 | Lowe | 260/78.3 |
| 2,703,316 | 3/1955 | Schneider | 260/78.3 |
| 3,878,284 | 4/1975 | Schmitt et al. | 264/184 |
| 4,033,938 | 7/1977 | Augurt et al. | 260/78.3 |
| 4,727,163 | 2/1988 | Bellis | 549/274 |
| 4,797,468 | 1/1989 | De Vries | 528/354 |
| 4,800,219 | 1/1989 | Murdoch et al. | 525/413 |
| 4,835,293 | 5/1989 | Bhatia | 549/274 |
| 4,895,681 | 1/1990 | Herrman et al. | 260/410 |
| 4,966,982 | 10/1990 | Ono et al. | 549/274 |
| 4,983,745 | 1/1991 | Muller et al. | 549/274 |
| 4,990,222 | 2/1991 | Aigner et al. | 203/91 |

FOREIGN PATENT DOCUMENTS

| | | |
|---|---|---|
| 0264926 | 4/1988 | European Pat. Off. |
| 3632103 | 3/1988 | Fed. Rep. of Germany |
| 3708915 | 9/1988 | Fed. Rep. of Germany |
| 3724933 | 2/1989 | Fed. Rep. of Germany |
| 9001521 | 2/1990 | World Int. Prop. O. |

*Primary Examiner*—C. Warren Ivy
*Assistant Examiner*—Amelia A. Owens
*Attorney, Agent, or Firm*—Charles E. Krukiel

[57] ABSTRACT

An improved process for the recovery of lactide or other dimeric cyclic ester from a gas stream containing the cyclic ester and such hydroxylic impurities as water and open-chain hydroxycarboxylic acids by scrubbing the gas stream with a nonpolar water-immiscible solvent at a temperature at which the cyclic ester is removed from the solvent and any water present in the gas stream is vaporized from the solvent. The cyclic ester is recovered from the solvent in a high state of optical purity.

19 Claims, No Drawings

1

SOLVENT SCRUBBING RECOVERY OF LACTIDE AND OTHER DIMERIC CYCLIC ESTERS

FIELD OF THE INVENTION

This invention relates to a solvent scrubbing process for the recovery of dimeric cyclic esters from impure reaction product streams. In particular the present invention relates to such recovery of the cyclic esters from gas product streams also containing water as an impurity by scrubbing with a non-polar water immiscible solvent, more particularly counter currently, at a temperature at which the cyclic ester is soluble in the solvent and any water present in the gas stream is vaporized from the solvent.

BACKGROUND OF THE INVENTION

The preparation of dimeric cyclic esters of alpha-hydroxycarboxylic acids is an old and much studied process. The preparation is normally conducted in two stages involving first preparing an oligomer of the hydroxycarboxylic acid, i.e., a relatively short-chain condensation polymer thereof, then heating the oligomer to depolymerize it to the desired cyclic ester. The preparation of dimeric cyclic esters is discussed in Gruter et al., U.S. Pat. No. 1,095,205 (1914); Lowe, U.S. Pat. No. 2,668,162 (1954); Bhatia, U.S. Pat. No. 4,835,293 (1989); Bellis U.S. Pat. No. 4,727,163 (1988); Muller, Ger. Pat. Application Publication Nos. 3632103 and 3708915 (1988). In the preparation of the oligomers from the corresponding alpha-hydroxycarboxylic acids the water of condensation is difficult to completely remove from the polymer. Water is also formed in the depolymerization step so that the cyclic ester depolymerization product generally contains water as an impurity. The cyclic ester may also contain one or more open-chain hydroxycarboxylic acids as impurities. All such hydroxylic impurities are undesirable as they act as chain-stoppers in the subsequent polymerization of the cyclic ester to the high molecular weight products required for biomedical and other uses. It is therefore desired to keep the water and open-chain hydroxycarboxylic acid content of the dimeric cyclic ester as low as practicable.

U.S. Pat. No. 4,835,293, to Bhatia discloses an improved depolymerization and product recovery process for the production of dimeric cyclic esters such as lactide wherein a stream of an inert gas is employed to strip the cyclic ester from the reaction zone along with any water and/or volatile hydroxycarboxylic acid also formed therein. The resulting gaseous product stream is scrubbed with a polar organic solvent to recover the cyclic ester. The solvents include alcohols, ethers, esters and ketones, with use of isopropyl alcohol exemplifying the recovery of glycolide from its impurities. Isopropyl alcohol as scrubbing solvent solubilizes the hydroxycarboxylic acids and any water present, thereby enabling the recovery of glycolide directly from the scrubbing medium as a substantially insoluble filterable crystalline solid.

Use of an alcohol, however, as the scrubbing solvent for the recovery of glycolide, lactide or other such cyclic ester from a vapor product stream is not entirely satisfactory. It as well as water can react in the alcoholic solution to form open-chain products, which not only constitute a yield loss but further tend to increase the solubility of the cyclic ester in the scrubbing solution, further aggravating the yield loss problem.

On the other hand, use of a non-hydroxylic polar scrubbing solvent such as acetone, for example, which is non-reactive towards dimeric cyclic esters and in which the esters are highly soluble, likewise presents difficulties inasmuch as such polar solvent solubilizes the by-product hydroxycarboxylic acids as well, so that further processing would be required to separate the cyclic ester from the acids.

Water as a scrubbing solvent is also unsatisfactory in that heat transfer to it is much faster then mass transfer; consequently, the cyclic ester precipitates as a fog of particles, difficult to capture in the absence of specialized and costly equipment.

Thus, a need exists for a means that provides for the substantially complete recovery of a cyclic ester such as lactide from a vapor stream that also contains open-chain acids as well as water. A need also exists for such process that also provides for the substantially complete recovery of the acid values as cyclic ester.

SUMMARY OF THE INVENTION

In the gas-assisted process for depolymerizing an oligomeric poly(hydroxycarboxylic acid) to a dimeric cyclic ester, which process comprises:

(1) heating the oligomer in a reaction zone at a suitable temperature and pressure and for a time effective to generate the cyclic ester, (2) passing a stream of an inert gas through the oligomeric material at a rate and in an amount sufficient to sweep the cyclic ester and any water present from the reaction zone and to form a gas stream containing the cyclic ester and any water entrained therewith, and (3) scrubbing the gas stream with a solvent to remove the cyclic ester therefrom, the improvement wherein:

(a) the solvent is nonpolar and water-immiscible, and preferably is a solvent for the cyclic ester at least at one temperature and is a non-solvent for water at said temperature, (b) scrubbing step (3) is conducted at a first temperature which is below the temperature of (a) and at which the solvent is liquid, the cyclic ester is removed from the gas stream and the temperature is such that any water removed from the gas stream forms an aqueous phase separate from the solvent phase containing cyclic esters, and (c) the solvent phase containing the cyclic ester is recovered.

In a preferred embodiment, the solvent is selected such that the cyclic ester is soluble and water substantially insoluble therein at the first temperature and the cyclic ester is a solid substantially insoluble in the solvent at a second, lower temperature. The solvent-cyclic ester phase is separated from the aqueous phase at the first temperature. The solvent-cyclic ester phase is cooled to the second, lower temperature to precipitate the cyclic ester and the precipitate is recovered, as by filtration or centrifugation.

In another preferred embodiment, the scrubbing temperature is such that the water is thus vaporized at said temperature and removed from the solvent.

In still another embodiment the scrubbing step is carried out counter-currently.

In other, more specific embodiments the oligomer is a relatively low molecular weight polymer of glycolic and/or lactic acid, including aqueous lactic acid such as the 80–90% acid available commercially, and the scrubbing solvent is an aliphatic, cycloaliphatic, aromatic hydrocarbon or halocarbon, preferably boiling in the range of from about 90° to about 200° C.

DETAILED DESCRIPTION OF THE INVENTION

The invention is applicable to the treatment of impure dimeric cyclic esters containing hydroxylic impurities such as water and open-chain hydroxycarboxylic acids. It is particularly applicable to the treatment of a vapor stream containing the impure cyclic ester, more particularly where the impure cyclic ester is a lactide composition. The invention process broadly comprises contacting a gas stream containing a dimeric cyclic ester as defined above and water, as an impurity, with a nonpolar solvent as defined above in an amount and at a temperature at which the cyclic ester is removed from the gas stream and the water is volatized therefrom, thereby effecting separation of the cyclic ester from the water impurity. Preferably the solvent is such that the cyclic ester is soluble therein. The cyclic ester is then separated from the solvent by any means known to the art, including evaporation of the solvent or crystallization of the cyclic ester from the solvent followed by filtration or centrifugation.

The gas stream containing the impure dimeric cyclic ester may be that generated in a gas-assisted depolymerization process as described by Bhatia in U.S. Pat. No. 4,835,293, which disclosure is incorporated herein by reference. In general such gas-assisted depolymerization process comprises heating an oligomer of an alpha-hydroxycarboxylic acid, (e.g. glycolic, lactic or mixed glycolic and lactic acids), to a temperature at which the oligomer is molten and depolymerizable to the corresponding dimeric cyclic ester, usually and preferably in the presence of a depolymerization catalyst, while passing an inert gas through the molten oligomer in an amount and at a rate sufficient to entrain the cyclic ester from the reaction mass, preferably as fast as it is formed. The resulting gas product stream normally also contains water and other volatile materials such as open-chain carboxylic acids.

In accordance with the present invention, a gas stream generated in the above referenced depolymerization process is scrubbed with a non-polar organic solvent as defined above in order to remove the cyclic ester from the gas stream and thereby separate the cyclic ester from any water present in the stream. The scrubbing solvent may be any normally liquid substance that is non-solvent for water at the operating temperature and has a normal boiling point of at least about 90° C., preferably at least about 130° C., more preferably at least about 150° C. but practically speaking not greater than about 230° C., preferably not greater than about 200° C. "Non-solvent" for water at the operating temperature refers to a solvent from which water will flash off and pass out of the scrubbing zone as a vapor stream. Preferably the solvent is selected such that the cyclic ester is soluble at the operating temperature and substantially insoluble at temperatures substantially below the operating temperature, e.g. at room temperatures to facilitate the recovery of the cyclic ester therefrom.

Suitable to this purpose are aliphatic, cycloaliphatic, aromatic hydrocarbon and halocarbon solvents exemplified by heptane, decane, decene, methylcyclohexane, toluene, o-,m- and p-xylene, cumene (isopropylbenzene), ethylbenzene, o-, m- and p-diethylbenzene, n-, sec- and isobutylbenzene, m-propyltoluene, p-propyltoluene, 1,2,4-trimethylbenzene (pseudocumene), chlorobenzene, o-, and m-dichlorobenzene, 1,2,4-trichlorobenzene and mixtures of one or more thereof. The aromatics are preferred for their greater solvency for the cyclic esters.

The operating temperature, that is, the temperature at which the scrubbing medium is maintained during the cyclic ester stripping operation, can vary widely depending on the particular cyclic ester and solvent involved. The temperature of the liquid scrubbing medium should be at least about as high as the melting point of the cyclic ester being recovered to reduce the possibility of the scrubber becoming clogged with solids. The temperature should also be sufficiently high to drive the water overhead and preferably solubilize the cyclic ester substantially completely. At the same time it should be lower than the boiling point of the cyclic ester as well as of the scrubbing solvent to avoid loss of the ester in the aqueous phase overhead. Preferably, it will be 15° below the solvent's boiling point, more preferably at least 25° below the boiling point. The temperature will normally be at least 70° and not more than about 180° C., more usually from about 90° to 150° C.

The pressure throughout the scrubbing step may vary from sub-atmospheric to atmospheric and super-atmospheric. Conveniently and preferably it will be about atmospheric pressure.

The process of the present invention is applicable to the recovery of dimeric cyclic esters having the following formula:

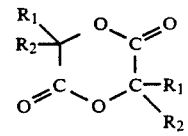

where each R group is independently H or a $C_1$–$C_6$ hydrocarbyl or substituted hydrocarbyl radical. Preferably each R group is H or a $C_1$–$C_3$ alkyl group, more preferably H or methyl. Typical dimeric cyclic esters include glycolide ($R_1=R_2=H$), lactide ($R_1=H$, $R_2=CH_3$) tetramethylglycolide, sym-diethylglycolide, the dimeric cyclic ester of alpha-hydroxyvaleric acid and the like. Preferred cyclic esters are glycolide, lactide (including L-, D- and meso-lactide) and mixtures of glycolide with one or more of the isomeric lactides.

The steps of polymerizing the alpha-hydroxycarboxylic acid to an oligomer and of depolymerizing the oligomer to a cyclic ester are ordinarily and preferably conducted in the presence of a catalyst. The catalyst can be any of those known in the art for promoting condensation of the alpha-hydroxycarboxylic acid to oligomers and for promoting cyclic ester formation. The catalysts are generally metals or compounds of metals of groups IV, V and VIII of the Periodic Table. Preferred catalysts are metals of groups IV, notably Sn as the metal (powdered), oxide, halogenide or carboxylate, or V, notably Sb, usually as the oxide $Sb_2O_3$. Particularly preferred catalysts are Sn(II) carboxylates, exemplified by Sn bis(2-ethylhexanoate), commonly referred to as stannous octoate.

The catalyst is employed in catalytically effective amounts, which can vary widely depending upon reaction conditions. The optimum catalytically effective amounts for any particular system can readily be determined through trial runs.

The gaseous agent for entraining/carrying/sweeping the cyclic ester and the impurities out of the reaction mixture and out of the depolymerization reactor may be any substance that is gaseous, stable and non-reactive at the operating temperatures and pressures and is inert to the starting material, reaction mass components and reaction products. It may be normally gaseous, such as nitrogen, argon, carbon monoxide or dioxide or low molecular weight hydrocarbon. It may be normally non-gaseous but gaseous at reaction temperature and pressure. Preferred is nitrogen for its inertness and ready availability. Preferably the inert gas will be preheated to the operating temperature and will be injected below the surface of the reaction mass in the reaction zone; for example, below the agitator of a stirred tank reactor or at the bottom of a vertically disposed reactor.

The flow rate of the gas should be sufficiently high so as not to limit the cyclic ester stripping rate. If the flow rate is too low, the conversion to cyclic ester may be adversely affected and its production rate limited since the gas functions importantly to carry the cyclic ester as vapor out of the reactor.

The depolymerizer reactor design is not critical provided the reactor has means for introducing an oligomeric feed stream, means for introducing a gaseous cyclic ester stripping agent into the reaction zone such that the stripping agent directly and intimately contacts the oligomeric composition so as to give high gas-liquid interfacial contact and has means for removing a gaseous stream containing cyclic ester. Thus, the reactor may be a stirred tank equipped with gas-sparging means, preferably one which admits the gas directly under the agitator. The reactor may also be a packed or sieve-plate column, or the reactor may be of any other design known in the art for effecting intimate gas-liquid contact.

Preferably, the depolymerization step is conducted in a continuous manner with the oligomer being fed continuously to the reactor at a controlled rate such that hold-up of polymeric material within the reactor is minimized. Continuous depolymerization of the oligomer minimizes degradation of the oligomer into any unwanted by-products and maximizes conversion of the oligomer into the desired cyclic ester. Thus, treating a gas stream from such a continuous depolymerization process by the present invention method would yield a still higher quality cyclic ester product.

EXAMPLES

The following examples were conducted in an apparatus comprising a gas-assisted depolymerization unit in association with a counter current scrubbing unit.

The depolymerization unit consisted essentially of a stirred 1000 ml tank having a gas inlet terminating at a point below the stirrer blade and a gas exit line leading to a 1" by 16" scrubbing column and entering the column just below its midpoint. The column surmounted a 1000 ml first receiver vessel and was connected at its upper end to a 4" head leading to downwardly arranged water cooled condenser emptying into a vented second reciever. The first receiver was fitted with an external tubular means leading via a pump to the top of the column so that liquid from the first receiver could be circulated up to the top of the column and allowed to flow downwardly through the column in contact with upcoming vapor stream. The column was packed with short sections of glass tubing below the gas inlet point and with glass beads above it. The stirred tank, the gas inlet and outlet, the column, the first receiver and the liquid circulating line were all fitted with thermocoupled heating means (mantles and tapes) for maintaining temperatures throughout the system. The head at the top of the column was unheated. Temperatures where noted are in degrees Celsius.

EXAMPLE 1

A. Lactic Acid Oligomer Preparation 750 grams of 88% L-lactic acid containing 2.5 g of stannous octoate was gradually heated under agitation while a stream of $N_2$ gas preheated to 100° C. was passed through it at a rate of 1500 standard cubic centimeters per minute (sccm). The temperature reached 92° in about 30 minutes and water started coming over. After 120 min at 92° the temperature was raised to 120° and held there for 160 min longer before being increased to 140°. After 75 min at 140° when lactide began to be evolved, the temperature was rapidly increased to 170° and held for about 5 min. A total of 190.1 g of water was collected during the above heating period.

B. Gas-Assisted Depolymerization and Counter Current Scrubbing Removal of L-Lactide from the Gas Product Stream.

The polylactic acid (oligomer) from (A) was heated to 215° C. while a stream of $N_2$, preheated to 140° C. was passed through it at a rate of 1500 sccm. Cumene was fed into the $N_2$ stream at a rate of 0.4 cc/min. over a 3 hr period. During this time the gas feed line to the column was held at 104°–110°, the first receiver at 110°–120°, the circulating line at 99°–100°, the column section below the gas feed line at 103°–105° and the section above the gas feed line at 114°–130° C. (sufficiently high to ensure that any water in the column would be in the vapor state but not so high as to completely vaporize the cumene). The temperature in the unheated column head was 92°–96°.

After the first and second hours of operation about 200 cc of cumene was added each time to the first receiver to ensure the presence of sufficient cumene for counter current flow down through the column.

The lactide that accumulated in the first receiver as a cumene solution was recovered by cooling the solution to room temperature. The resulting off-white precipitate was filtered, washed twice with isopropyl alcohol and dried under reduced pressure to yield highly pure white crystalline L-lactide (52 g) having an optical rotation of −297 versus −300 reported.

The cumene filtrate was water-free but yellow in color, indicating the presence of unsaturated decomposition products formed in the depolymerization step. The residue in the cracking pot was amber in color and weighed 366 g. The second receiver contained a two-phase mixture of water and cumene.

EXAMPLE 2

This example illustrates a process wherein aqueous lactic acid is dehydrated, converted to oligomer, the oligomer is depolymerized to lactide in a stream of carrier gas and the lactide depolymerization product is counter currently stripped from the gas product stream and recovered as a bottoms solution in the stripping solvent while water is removed as overhead.

The procedure of Example 1 was repeated except that the L-lactic acid-stannous octoate composition was heated in the depolymerization unit described above such that the lactic acid dehydration and oligomerization steps were conducted as essentially described in Section A above and the depolymerization step was conducted essentially as in Section B above. The optical rotation of the L-lactide product was −294°.

It will be noted that feeding the scrubbing solvent in the gaseous entraining agent as exemplified above aids into stripping the cyclic ester from the oligomeric material as well as providing recirculating liquid for countercurrently stripping the cyclic ester from the gas product stream. However, it can be omitted from the gas feed stream provided the first receiver contains sufficient scrubbing solvent to be recirculated up to and down the column so as to countercurrently contact the upcoming gas stream containing the cyclic ester and its hydroxylic impurities.

EXAMPLE 3

L-lactic acid oligomer was prepared from 752.4 grams of 88% L-lactic acid essentially as described in Example 1, part A above; 195 grams of water were collected. The oligomer was heated under agitation at 216°–230° C. for about 2.5 hours with a stream of $N_2$ passing through it at a rate of 0.35 standard cubic foot per minute, during which time the gas stream was passed into a 1000 ml receiver containing charge of toluene as the scrubbing medium and surmounted by a water-cooled condenser. An additional 300 ml of toluene was added to the scrubber after 1 hour followed by 500 ml of toluene 0.75 hour later to compensate for vaporization of solvent from the receiver. The temperature of the gas stream ranged from a brief (0.25 hour) low of 95° at the beginning through a long (almost 2-hour) range of 128°–156° C., mostly above 140° C., to a brief (about 0.25 hour) final low of 121° C. The temperature of the toluene scrubbing medium during this time ranged from an initial 83° C. through a high of 127° C. to a final 93° C.

The toluene solution was cooled to below room temperature and filtered. The filter cake (199.5 g) was washed with toluene and dried under reduced pressure (183.7 g dry weight). The dry product had a purity of 97.8 determined by differential scanning calorimetry (DSC).

We claim:

1. In the gas-assisted process for depolymerizing an oligomeric poly(hydroxycarboxylic acid) to a dimeric cyclic ester of the formula (I):

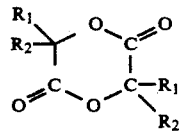

wherein each R group is independently H or a $C_1$–$C_6$ hydrocarbyl, which process comprises:
   (a) heating the corresponding oligomer in a reaction zone at a suitable temperature and pressure and for a time effective to generate the cyclic ester;
   (b) passing a stream comprising an inert gas through the oligomeric material at a rate and in an amount sufficient to sweep the cyclic ester and any water present from the reaction zone and to form a gas stream containing the cyclic ester and any water entrained therewith; and
   (c) scrubbing the gas stream with a solvent to remove the cyclic esters therefrom, the improvement comprising:
      (i) the solvent is nonpolar and water-immiscible,
      (ii) scrubbing step (c) is conducted at a first temperature which is below said suitable temperature of step (a) and at which the solvent is liquid, the cyclic ester is removed from the gas stream to form a phase comprising the cyclic ester and solvent, and is such that any water removed from the gas stream forms an aqueous phase separate from the solvent and cyclic ester phase, and
      (iii) the phase containing the solvent and cyclic ester is recovered.

2. The process of claim 1 wherein the first temperature is at least about as high as the melting point of the cyclic ester, and is sufficiently high to vaporize at least a portion of the water from the phase containing the cyclic ester.

3. The process of claim 1 wherein the cyclic ester is separated from the solvent phase of step c (iii).

4. The process of claim 1 wherein the solvent comprises a solvent for the cyclic ester as said first temperature.

5. The process of claim 4 wherein the polar solvent is a relatively poor solvent for the cyclic ester at a second temperature which is lower than the first temperature, the cyclic ester comprises a solid substantially insoluble in the solvent at the second temperature, the solvent phase containing the cyclic ester is cooled to about the second temperature to precipitate the cyclic ester and the cyclic ester is separated from the solvent.

6. The process of claim 1 wherein the scrubbing solvent is countercurrently contacted with the gas stream.

7. The process of claim 2 wherein the scrubbing solvent boils in the range of about 90° to about 230° C. and the scrubbing temperature is in the range of about 70° to about 180° C.

8. The process of claim 7 wherein the scrubbing solvent boils in the range of about 130° to about 200° C. and the scrubbing temperature is in the range of from about 90° to 150° C.

9. The process of claim 7 wherein the solvent comprises at least one of an aromatic hydrocarbon and a halocarbon.

10. The process of claim 9 wherein the solvent comprises cumene and the scrubbing temperature is in the range of about 95° to 135° C.

11. The process of claim 1 wherein each R group is H or a $C_1$–$C_3$ alkyl group.

12. The process of claim 11 wherein R comprises at least one $C_1$–$C_3$ alkyl group.

13. The process of claim 12 wherein the cyclic ester comprises at least one of glycolide and lactide.

14. The process of claim 13 wherein the cyclic ester comprises L-lactide.

15. The process of claim 1 wherein said oligomer of step (a) is formed "in situ" in the reaction zone by directly feeding an alpha-hydroxycarboxylic acid to the reaction zone and heating said acid at a temperature and pressure and for a time effective to convert said acid to said oligomer.

16. The process of claim 1 wherein the inert gas comprises at least one gas selected from the group consisting of nitrogen, argon, carbon monoxide, carbon dioxide and a low molecular weight hydrocarbon.

17. The process of claim 3 wherein said separation is performed by crystalizing the cyclic ester.

18. The process of claim 1 wherein said solvent comprises at least one solvent selected from the group consisting of aliphatic, cyclic aliphatic, aromatic hydrocarbon and halocarbon solvents.

19. A process for producing a cyclic ester comprising:

forming an oligomer from an alphahydroxycarboxylic acid;

heating said oligomer, while in the presence of a catalyst, to a temperature at which said oligomer depolymerizes into a cyclic ester;

passing an inert gas through said oligomer to provide a stream which entrains at least a portion of said cyclic ester;

scrubbing said stream with a non-polar solvent to remove at least a portion of said entrained cyclic ester from said stream;

and separating the ester from the solvent.

* * * * *